United States Patent [19]

Smith et al.

[11] Patent Number: 4,710,177
[45] Date of Patent: Dec. 1, 1987

[54] SUBCUTANEOUS VENTRICULAR INJECTION APPARATUS AND METHOD

[76] Inventors: Robert R. Smith, 2574 Lake Cir., Jackson, Miss. 39211; Thomas B. Briggs, 238 E. Lorenz Bldg., Jackson, Miss. 39216

[21] Appl. No.: 863,419

[22] Filed: May 15, 1986

[51] Int. Cl.$^4$ ............................................. A61M 1/00
[52] U.S. Cl. ........................................ 604/185; 604/9; 604/249; 604/153; 128/912
[58] Field of Search ................... 604/185, 175, 236, 9, 604/27, 249, 323, 350, 153, 212; 128/912

[56] References Cited

U.S. PATENT DOCUMENTS

| | | | |
|---|---|---|---|
| 3,310,051 | 3/1967 | Schulte . | |
| 3,492,996 | 2/1970 | Fountain . | |
| 3,503,402 | 3/1970 | Schulte | 604/185 |
| 3,527,220 | 6/1968 | Summers . | |
| 3,527,226 | 9/1970 | Hakin | 604/185 |
| 3,827,439 | 8/1974 | Schulte et al. | 604/185 |
| 3,951,147 | 4/1976 | Tucker et al. . | |
| 3,971,376 | 7/1976 | Wichterle . | |
| 4,350,155 | 9/1982 | Thompson . | |
| 4,464,168 | 8/1984 | Redmond et al. | 604/9 |
| 4,548,607 | 10/1985 | Harris | 604/153 |
| 4,549,879 | 10/1985 | Grashing et al. | 604/9 |
| 4,560,375 | 12/1985 | Schulte et al. | 604/9 |

OTHER PUBLICATIONS

"Cancer Pain Relieved by Long-Term Epidural Morphine with Permanent Indwelling Systems for Self-Administration", by Charles E. Polleti, M. D. et al.; Oct., 1981.
"Intraventricular Administration of Morphine in Patients with Neoplastic Intractable Pain", by B. Roquefeuil, et al.; 1984.

Primary Examiner—John D. Yasko
Assistant Examiner—Denise Whelton
Attorney, Agent, or Firm—Larson and Taylor

[57] ABSTRACT

An injection system and method for delivering fluids to a subcutaneous body site such as an analgesic to the ventricle is disclosed. A reservoir containing a plurality of doses of the fluid is adapted to be subcutaneously located in the abdomen. This reservoir is connected by a catheter to a subcutaneous unit containing a valve and a pump. This unit is then connected to the ventricle of the user. By the simultaneous actuation of the valve and the pump, the analgesic is pumped to the ventricle of the user. Preferably, the reservoir includes an expandable bag and a bubble member on the outermost surface of the bag which is penetrable by a small needle on the outersurface and impenetrable on the innersurface. A fluid passageway then connects the bag and the bubble member so that the bag is easily refilled. The pump and valve are preferably operated by flexible portions on the subcutaneous unit, which flexible portions are preferably recessed to prevent inadvertent actuation. A tap reservoir provided on the catheter leading to the ventricle is also preferably provided in order to inject additional fluids to flush the system or to sample the fluids in the ventricle.

14 Claims, 4 Drawing Figures

SUBCUTANEOUS VENTRICULAR INJECTION APPARATUS AND METHOD

FIELD OF THE INVENTION

The present invention relates generally to the subcutaneous injection of a fluid or the like, and more particularly to a subcutaneous ventricular injection apparatus and method for injecting morphine and the like to the ventricle.

BACKGROUND OF THE INVENTION

It has been disclosed in the prior art that intraventricular administration of morphine in patients with neoplastic intractable pain is both possible and efficient. Such a method is disclosed in "Intraventricular Administration of Morphine in Patients with Neoplastic Intractable Pain" by D. Roquefeuil et al, *Surgical Neurology*, 1984; 21:155-8. As shown in this article, an externally hung collecting bag was connected to the ventricle of the user by a catheter which entered the body at the neck region. A Cordis valve unit was provided on the external catheter such that 50 mg could be administered into the ventricle each time the valve unit was open.

Another system for relieving cancer pain by the administration of morphine using an indwelling system is disclosed in "Cancer Pain Relieved by Long-Term Epidural Morphine With Permanent Indwelling Systems for Self-Administration" by C. Poletti et al, *Journal of Neurosurgery*, Vol. 55, October 1981, pages 581-584. One of the systems disclosed includes a completely indwelling catheter system consisting of a morphine reservoir, a shunt pump, and on-off valve. The morphine was administered to the spinal epidural space.

Various implantable devices for delivering fluids to a portion of the body have been disclosed in prior patents. For example, in U.S. Pat. No. 3,310,051 (Schulte), a surgical implant consisting of a capsule acting as a reservoir for fluids is disclosed. A tube communicates the fluid to regions of the brain. In U.S. Pat. No. 3,527,220 (Summers), a blader and pump system which is implanted in the abdomen in order to administer drugs and other substances to various parts of the body is disclosed. The pump is driven by a magnet located outside of the body. A surgically implantable device for relieving fluid pressure on the brain is disclosed in U.S. Pat. No. 3,492,996 (Fountain). The device disclosed includes a ventriculo-atrial shunt which comprises an elbow catheter attached to a dual pump/valve device implanted under the scalp. The pumping device is a substantially flat, flexible plate adapted to overlie the skull and has a pair of bubble-shaped chambers positioned thereon and adapted for finger manipulation to provide pumping action to clear the conduits of obstructions.

Various other devices have been disclosed in the prior art for internally administering drugs or fluids to various regions of the body. In U.S. Pat. No. 3,971,376 (Wichterle) and U.S Pat. No. 3,951,147 (Tucker et al), implanted devices are disclosed which can be refilled by injection with a hypodermic needle. A body implantable medical infusion system is also disclosed in U.S. Pat. No. 4,350,155 (Thompson).

SUMMARY OF THE INVENTION

In accordance with the present invention, an apparatus and method for delivering a fluid to a subcutaneous body site is provided. A reservoir containing a plurality of doses of the fluid is subcutaneously located, such as in the abdomen area. A subcutaneous catheter means is then provided for connecting the reservoir with the body site, such as the ventricle of the user. A subcutaneous pump means is also provided adjacent the body site and is fluidly disposed between the end of the catheter means in the body site and the reservoir. The pump means is manually pumped to deliver measured amounts of the fluid from the reservoir to the end of the catheter in the body site. A resiliently biased closed subcutaneous valve means is also located adjacent the pump means and is fluidly disposed between the end of the catheter means and the reservoir. This valve means allows the flow of fluid through the catheter means only when the valve means is manually held in the open position during simultaneous operation of the pump means.

In the preferred embodiment of the present invention, the reservoir is refillable by use of of hypodermic needle or the like. The reservoir preferably includes an expandable bag with a bubble member on an outermost surface of the bag which is palpable beneath the skin of the user. The bubble member has a front wall which is penetratable by a small needle and which reseals itself after such a penetration. A back wall of the bubble member is also provided which is impenetrable by a small needle. A fluid passageway is provided between the bag and the bubble member so that filling of the bubble member results in filling of the bag.

Preferably, the pump means and valve means are formed as a single unit which is implanted under the scalp of the user for delivering an intraventricular analgesia. The unit includes a first flexible portion which is depressed by the user to open the valve means and a second flexible portion which is depressed by the user to operate the pump means. The valve means is preferably a resilient planar member having a central slit therein which is normally closed and a cross member which is extends laterally across the slit. With this construction, when the cross member is moved into the plane of the planar member by movement of the first flexible portion, the slit is caused to open and allow fluid flow through the unit. The pump means preferably includes a central chamber beneath the second flexible portion. An inlet to this chamber contains a spring operated one-way valve means for admitting fluid into the chamber and an outlet contains the spring operated one-way valve means for passing fluid out of the chamber. For easy placement, the unit preferably includes a flat back portion. In order for the user to easily find the flexible portions, these portions are preferably recessed for the remainder of the front of the unit.

In the preferred embodiment, the catheter means also includes a tap reservoir which is located downstream of the pump means and valve means. The tap reservoir includes an outermost surface which is penetrable by a small needle and which reseals itself after such a penetration. An innermost surface of the tap reservoir is also provided which is impenetrable to a small needle. Thus, the tap reservoir can be used to add additional fluids to the fluid delivered to the body site to sample fluids at the body site, and to flush the injection system.

It is an advantage of the present invention that the injection system is totally subcutaneous once implanted.

It is also an advantage of the present invention that the implanted injection system is refillable by a hypodermic needle or the like when the reservoir becomes depleted.

It is a further advantage of the present invention that the pump means of the injection system cannot be inadvertently actuated as the pump means will not function unless the valve means is also simultaneously actuated. Thus, actuation of the injection system requires a conscious effort using both hands of the user which cannot occur accidentally.

Other features and advantages of the present invention are stated in or apparent from a detailed description of a presently preferred embodiment of the invention found hereinbelow.

DETAILED DESCRIPTION OF THE PREFERRED EMBODIMENT

Figure 1:
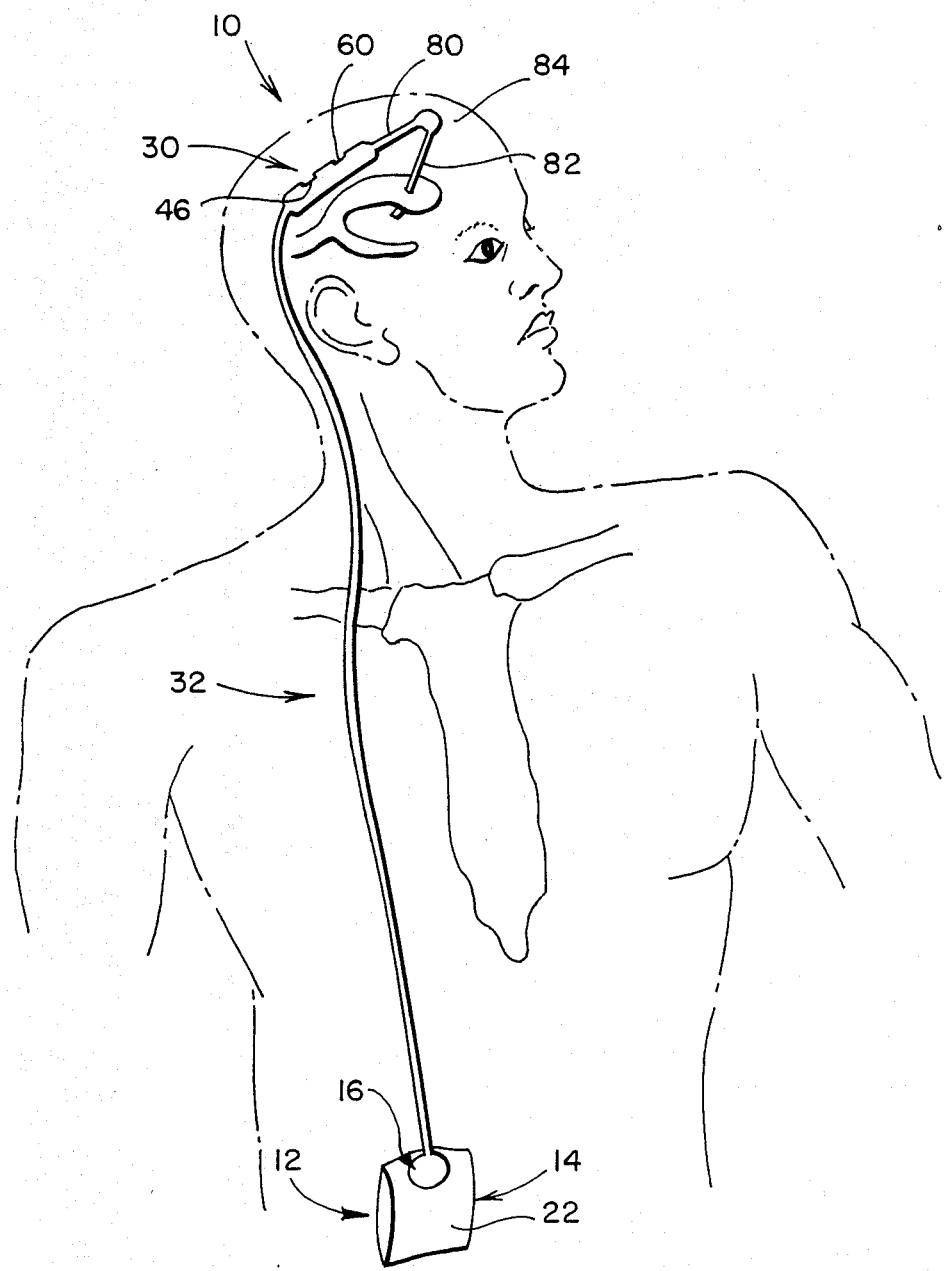
FIG. 1 is a schematic depiction of the injection system of the present invention arranged to deliver an analgesic to the ventricle of a user.
Figure 2:
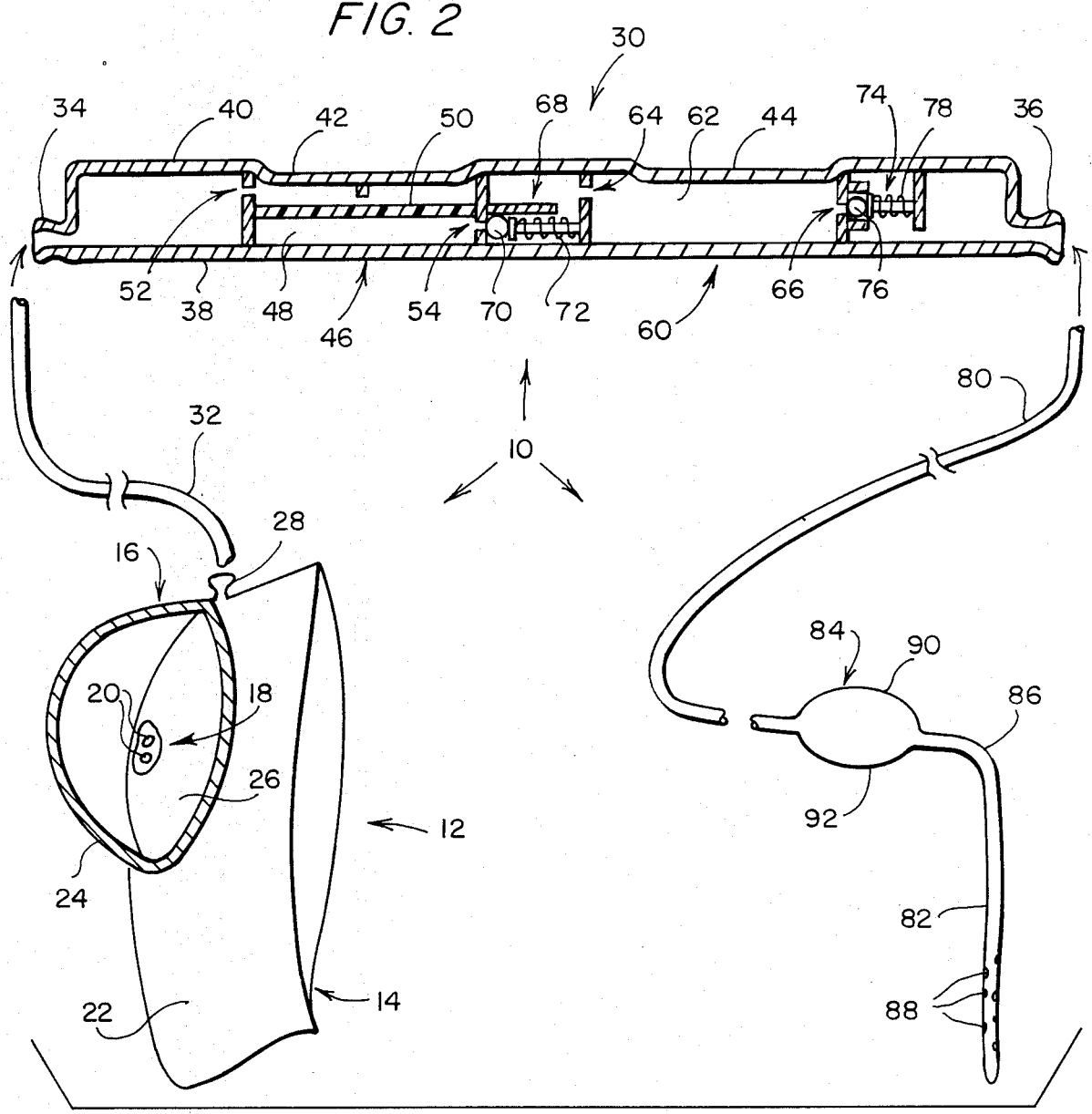
FIG. 2 is a schematic representation of the elements of the present invention, some of which are in cross section.

With reference now to the drawings in which like numerals represents like elements throughout the several views, an injection system 10 according to the present invention is depicted in FIGS. 1 and 2. Injection system 10 includes a reservoir 12 containing a plurality of doses of a fluid to be delivered to a body site of the user. For example, reservoir 12 could contain morphine or a similar intraventricular analgesic which is to be delivered to the ventricle of the user to relieve pain. For convenience, reservoir 12 is located subcutaneously in the abdominal area of the user. Reservoir 12 includes a large expandable bag 14 and a smaller bubble member 16 thereon. Bubble member 16 is fluidly connected to expandable bag 14 by a passageway 18 comprised of two holes 20.

As shown in FIG. 1, bubble member 16 is located on an outermost surface 22 of expandable bag 14 such that bubble member 16 is palpable beneath the skin of the user. Bubble member 16 includes a front wall 24 which is penetrable by a small needle and which reseals itself after such a penetration. Behind front wall 24, bubble member 16 includes a back wall 26 which is impenetrable to a small needle. Reservoir 12 is adapted to be located subcutaneously, and is therefore made of a suitable material such a silicon or the like. Preferably, reservoir 12 has a 100 cc to 200 cc capacity and a standard connector 28 for connection to standard VP shunt type tubing.

Reservoir 12 is connected to a subcutaneous unit 30 located under the scalp of the user by a suitable catheter means 32 such as a standard shunt tubing. Unit 30 includes an inlet connector 34 and an outlet connector 36 which are adapted to be easily connected to standard shunt type tubing. Unit 30 has a back portion 38 which forms a flat surface which is easily oriented during placement thereof. Front portion 40 of unit 30 includes a first flexible portion 42 and a second flexible portion 44.

Figure 3:
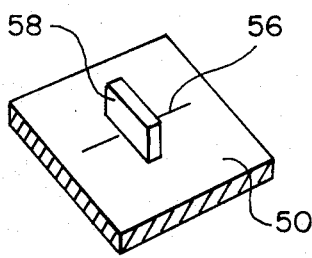
FIG. 3 is a schematic perspective view of a portion of the valve means of the present invention in a closed position.
Figure 4:
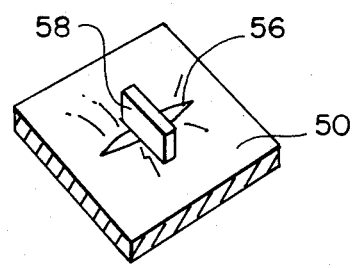
FIG. 4 is a schematic perspective view of a portion of the valve menas of the present invention in the open position.

First flexible portion 42 forms part of a valve means 46. Valve means 46 includes a chamber 48 which is divided in half by a resilient planar member 50. Chamber 48 then includes an inlet 52 in communication with inlet connector 34 and an outlet 54. As shown in FIGS. 3 and 4, planar member 50 includes a central slit 56. Located above slit 56 and extending perpendicular to the direction of slit 56 is a cross member 58. Cross member 58 is preferably attached to first flexible portion 42. As shown in FIG. 4, when first flexible portion 42 is pushed downwardly, cross member 58 contacts planar member 50 and causes slit 56 to open. However, the resilient bias of planar member 50 normally causes slit 56 to be closed as depicted in FIG. 3.

Subcutaneous unit 30 also includes a pump means 60. Pump means 60 has a central chamber 62 located beneath second flexible portion 44. Central chamber 62 includes an inlet 64 and an outlet 66. Located fluidly between outlet 54 of valve means 46 and inlet 64 of central chamber 62 is a one-way valve means 68. Preferably, one-way valve means 68 includes a ball 70 which is biased by a spring 72 against outlet 54 thereby sealing outlet 54. Thus, fluid can flow through one-way valve means 68 only from outlet 54 to inlet 64 when the force of spring 72 is overcome on ball 70.

A one-way valve means 74 is also provided at the other end of central chamber 62. One-way valve means 74 includes a ball 76 resiliently biased by a spring 78 into sealing contact with outlet 66. Thus, fluid flow is only allowed from central chamber 62 through outlet 66 when the bias of spring 78 against ball 76 is overcome and thus fluid flow is allowed to outlet connector 36.

Attached to outlet connector 36 of subcutaneous unit 3 is a catheter means 80. Catheter means 80 is connected to a ventricular catheter 82. Ventricular catheter 82 includes a tap reservoir 84 and a flexible elbow 86. At the distal end, ventricular catheter 82 includes a plurality of perforations 88. Tap reservoir 84 has an outermost surface 90 which is penetrable by a small needle and which reseals itself after such a penetration. Tap reservoir 84 also includes an innermost surface 92 which is impenetrable to a small needle.

In operation, injection system 10 functions in the following manner. Initially, injection system 10 is implanted on the user, for example to deliver calibrated doses of analgesics of the morphine and endorphine nature into the ventricular system of the brain. To accomplish this, reservoir 12 is implanted in the abdominal area of the patient while subcutaneous unit 30 is located under the scalp of the user. Reservoir 12 is implanted so that bubble member 16 is outermost and hence palpable beneath the skin of the user. Subcutaneous unit 30 is implanted such that back portion 38 which is flat is innermost and hence easily located. Reservoir 12 and subcutaneous unit 30 are connected by catheter means 32.

Catheter means 80 is also implanted in the user such that tap reservoir 84 is located under the scalp of the user adjacent a Burr hole located 2.5 cm from the midline and 9 cm above the glabella. Ventricular catheter 82 is inserted in the ventricular by use of a stylet which is placed through catheter means 80 and the catheter 82 in order to allow easy placement in the ventricle. For this reason, elbow 86 of ventricular catheter 82 must be flexible. Ventricular catheter 82 is approximately 8 cm long in order to have the proper placement of perforations 88 in the ventricle.

Once implanted, injection systems 10 is ready for use once expandable bag 14 is filled with a suitable analgesic fluid. Expandable bag 14 can be initially filled with this fluid during implantation if desired. Alternately, or whenever expandable bag 14 runs low on fluid, expandable bag 14 is filled in the following manner. A syringe containing the analgesic fluid is used to puncture bubble member 16 (through the skin) which is easily palpable beneath the skin of the user. The fluid from the syringe is then injected into bubble member 16 and passes through holes 20 into expandable bag 14. It should be appreciated that back wall 26 of bubble member 16 is impenetrable to small needle in order to prevent the small needle from passing through both front wall 24 and a back wall 26 of bubble member 16.

After expandable bag 14 is filled with the analgesic fluid, a predetermined dosage of the analgesic fluid is delivered to the ventricle of the user by usage of subcutaneous unit 30. It should be appreciated that subcutaneous unit 30 requires the simultaneous depression of both first flexible portion 42 and second flexible portion 44. Thus subcutaneous unit 30 is not accidentally actuated by the pressing of one flexible portion or the other. In addition, first flexible portion 42 and second flexible portion 44 are recessed from the remainder of front portion 40 of subcutaneous unit 30 to further minimize the possibility of accidental contact actuating valve means 46 or pump means 60. Thus, when it is desired to deliver a dose of analgesic fluid, first flexible portion 42 is depressed by the user. This causes cross member 58 to engage planar member 50 and cause slit 56, which is normally biased closed, to assume the open position as depicted in FIG. 4. Thus, depression of first flexible portion 42 causes a fluid pathway from inlet connector 34 to outlet 54 to be open.

After first flexible portion 42 is depressed, second flexible portion 44 is depressed one or a predetermined number of times to operate pump means 60. By depressing second flexible portion 44, the analgesic fluid contained in central chamber 62 is pressurized. This increase in pressure causes ball 76 to push against spring 78 and away from outlet 66 to allow the analgesic fluid in central chamber 62 to be conducted to perforations 88 of ventricular catheter 82. As second flexible portion 44 is released, the fluid in central chamber 62 is depressurized. This causes ball 70 to be pulled against spring member 72 opening outlet 54 and allowing the analgesic fluid from chamber 48 which is fluidly connected to reservoir 12 to flow through outlet 54 and to central chamber 62 until the pressure is equalized. Then, second flexible portion 44 is again capable of being actuated to pump another measured dosage of the analgesic fluid into the ventricle of the user.

If it is desired to flush injection system 10, to inject an additional fluid into the ventricle, or to sample fluids in the ventricle, tap reservoir 84 is used. Tap reservoir 84 includes an outermost surface 90 which is penetrable by a small needle. However, it should be appreciated that innermost surface 92 is not penetrable. Thus, using a simple hypodermic or the like, it is possible to inject or withdraw fluids from tap reservoir 84 for any of the purposes noted above. Where injection system 10 is flushed, operation of valve means 46 and pump means 60 also accompanies withdrawal of fluid from tap reservoir 84.

In the preferred embodiment of the present invention, pump means 60 delivers a predictable volume of fluid in fractions of a milliliter at each compression of second flexible portion 44. In addition, the various components are manufactured from tissue non-reactive silastic or stainless steel. In the preferred embodiment, catheter means 32 and 80 are also preferably made from a radio opaque tubing. The capacity of reservoir 12 is preferably approximately 100 cc to 200 cc.

Although the present invention has been described with respect to an exemplary embodiment thereof, it should be appreciated by those of ordinary skill in the art that variations and modifications can be effected within the scope and spirit of the invention.

We claim:

1. An injection system for delivering a fluid to a subcutaneous body site comprising:
   a reservoir containing a plurality of doses of the fluid, said reservoir adapted to be subcutaneously located;
   a subcutaneous catheter means for connecting said reservoir and the body site, siad catheter means including an end located at the body site;
   a subcutaneous pump means located adjacent the body site and fluidly disposed between the end of said catheter means and said reservoir for pumping measured amounts of the fluid from said reservoir to the end of said catheter means, said pump means including a first depressible member which is manually depressed to pump the fluid; and
   a subcutaneous valve means located adjacent said pump means and fluidly disposed between the end of said catheter means and said reservoir for blocking the flow of fluid through said catheter means even when said first depressible member of said pump means is depressed, said valve means including a resilient biasing means for resiliently biasing said valve means to the closed position and a second depressible member physically separated from said first depressible member which is manually depressed to overcome said resilient biasing means and open said valve means such that the flow of fluid through said catheter means is only accomplished when said first depressible member and said second depressible member are depressed simultaneously.

2. An injection system as claimed in claim 1 wherein said reservoir is refillable and includes:
   (a) an expandable bag,
   (b) a bubble member on an outermost surface of said bag which is palpable beneath the skin of the user, said bubble member having a front wall which is penetrable by a small needle and which reseals itself after such a penetration, and a back wall which is impenetrable to a small needle, and
   (c) a fluid passagewy provided between said bag and said bubble member.

3. An injection system as claimed in claim 1 wherein said pump means and said valve means are formed as a unit having an integral outer wall, said outer wall having a first flexible outer wall portion forming said second depressible member which is depressed by the user to open said valve means and a second flexible outer wall portion forming said first depressible member which is depressed by the user to operate said pump means.

4. An injection system as claimed in claim 3 wherein said valve means includes a resilient planar member having a central slit therein which is normally closed, and a cross member which extends laterally across said slit and which is moved into the plane of said planar member by movement of said first flexible portion to open said slit.

5. An injection system as claimed in claim 4 wherein said pump means includes a central chamber beneath said second flexible portion, an inlet containing a resiliently operated one-way valve means for admitting fluid into said chamber, and an outlet containing a resiliently operated one-way valve means for passing fluid out of said chamber.

6. An injection system as claimed in claim 5 wherein said unit includes a front portion containing said first flexible portion and said second flexible portion, and a back portion formed with a flat surface such that said unit is easily oriented during placement.

7. An injection system as claimed in claim 6 wherein said first flexible portion and said second flexible portion are recessed from the remainder of said front portion.

8. An injection system as claimed in claim 1 wherein said catheter means includes a tap reservoir located downstream of said pump means and of said valve means.

9. An injection system as claimed in claim 8 wherein said tap reservoir includes an outermost surface which is penetrable by a small needle and which reseals itself after such a penetration, and an innermost surface which is impenetrable to a small needle.

10. An injection system for delivering a fluid to a subcutaneous body site comprising:
    a refillable reservoir containing a plurality of doses of the fluid, said reservoir adapted to be subcutaneously located and including
    (a) an expandable bag,
    (b) a bubble member on an outermost surface of said bag which is palpable beneath the skin of the user, said bag having a front wall which is penetrable by a small needle and which reseals itself after such a penetration and a back wall which is impenetrable to a small needle, and
    (c) a fluid passageway provided between said bag and said bubble member;
    a subcutaneous catheter means for connecting said bag and the body site, said catheter means including an end at the body site;
    a subcutaneous pump means located adjacent the body site and fluidly disposed between the end of said catheter means and said reservoir for manually pumping measured amounts of the fluid from said reservoir to the end of said catheter means; and
    a valve means located adjacent said pump and fluidly disposed between the end of said catheter means and said bag for allowing the flow of fluid through said catheter means only when said valve means is manually opened.

11. An injection system for delivering a fluid to a subcutaneous body site comprising:
    a reservoir containing a plurality of doses of the fluid, said reservoir adapted to be subcutaneously located;
    a subcutaneous catheter means for connecting said reservoir and the body site, said catheter means including an end at the body site; and
    a subcutaneous unit fluidly disposed between said reservoir and the end of said catheter means and including
    (a) a pump means for manually pumping measured amounts of the fluid from said reservoir to the end of said catheter means, said pump means including a central chamber, an inlet containing a biased one-way valve means for admitting fluid into said chamber and an outlet containing a biased one-way valve means for passing fluid out of said chamber,
    (b) a biased valve means for allowing pumping of the fluid by said pumping means only when said valve means is manually held in the opened position, said valve means including a resilient planar member having a central slit therein which is normally closed and a cross member which extends laterally across said slit,
    (c) a first flexible portion which is depressed to push said cross member against said slit and thereby to open said slit, and
    (d) a second flexible portion which forms part of said central chamber and which is depressed to operate said pump means.

12. An injection system as claimed in claim 11 wherein said first flexible portion and said second flexible portion are formed as recesses on an outermost side of said unit, and wherein an innermost side of said unit is flat.

13. An injection system a claimed in claim 11 wherein said catheter means includes a tap reservoir located downstream of said pump means and of said valve means, said tap reservoir including an outermost surface which is penetrable by a small needle and which reseals itself after such a penetration and an innermost surface which is impenetrable to a small needle.

14. An injection system as claimed in claim 13 wherein said reservoir is refillable and includes:
    (a) an expandable bag,
    (b) a bubble member on an outermost surface of said bag which is palpable beneath the skin of the user, said bubble member having a front wall which is penetrable by a small needle and which reseals itself after such a penetration, and a back wall which is impenetrable to a small needle, and
    (c) a fluid passageway provided between said bag and said bubble member.

* * * * *